US010653821B2

(12) United States Patent
Nichols

(10) Patent No.: US 10,653,821 B2
(45) Date of Patent: May 19, 2020

(54) HAEMOSTATIC DEVICE

(71) Applicant: SELENTUS SCIENCE LIMITED, Lincolnshire (GB)

(72) Inventor: John Benjamin Nichols, Grantham (GB)

(73) Assignee: SELENTUS SCIENCE LIMITED, Grantham (GB)

(*) Notice: Subject to any disclaimer, the term of this patent is extended or adjusted under 35 U.S.C. 154(b) by 0 days.

(21) Appl. No.: 15/768,400

(22) PCT Filed: Oct. 13, 2016

(86) PCT No.: PCT/GB2016/053176
§ 371 (c)(1),
(2) Date: Apr. 13, 2018

(87) PCT Pub. No.: WO2017/064495
PCT Pub. Date: Apr. 20, 2017

(65) Prior Publication Data
US 2018/0303980 A1    Oct. 25, 2018

(30) Foreign Application Priority Data
Oct. 14, 2015  (GB) .................... 1518182.9

(51) Int. Cl.
*A61L 31/16*    (2006.01)
*A61L 31/14*    (2006.01)
(Continued)

(52) U.S. Cl.
CPC ...... *A61L 31/146* (2013.01); *A61F 13/00021* (2013.01); *A61L 15/425* (2013.01);
(Continued)

(58) Field of Classification Search
CPC ....... A61K 38/00; A61L 24/00; A61L 31/146; A61L 15/32; A61L 15/425; A61L 15/64;
(Continued)

(56) References Cited

U.S. PATENT DOCUMENTS 5,836,970 A * 11/1998 Pandit .................. A61L 15/225
606/213
9,302,034 B2    4/2016 Corley
(Continued)

FOREIGN PATENT DOCUMENTS

CN    203122775    8/2013
JP    4476616    6/2010
(Continued)

OTHER PUBLICATIONS

Blood [online] retrieved on Apr. 11, 2019 from: https://www.britannica.com/science/blood-biochemistry; 13 pages. (Year: 2019).*
(Continued)

*Primary Examiner* — Ernst V Arnold
(74) *Attorney, Agent, or Firm* — Leber IP Law; Shelly M. Fujikawa

(57) ABSTRACT

A bioresorbable haemostatic foam sponge for adhering to a wound. The sponge has a tissue-contacting surface divided into a plurality of closely-spaced tissue contacting elements. Also disclosed are methods for forming the haemostatic sponge and methods of using the sponge.

20 Claims, 16 Drawing Sheets

(a)   (b)   (c)

(d)

(51) Int. Cl.
*A61L 15/42* (2006.01)
*A61L 15/64* (2006.01)
*A61F 13/00* (2006.01)
*A61L 15/32* (2006.01)

(52) U.S. Cl.
CPC ............ *A61L 15/64* (2013.01); *A61L 31/148* (2013.01); *A61L 31/16* (2013.01); *A61F 2013/00463* (2013.01); *A61L 15/32* (2013.01); *A61L 2300/418* (2013.01); *A61L 2400/04* (2013.01)

(58) Field of Classification Search
CPC ........... A61L 2300/418; A61L 2400/04; A61L 31/148; A61L 31/16; A61F 13/00021; A61F 2013/00463
See application file for complete search history.

(56) References Cited

U.S. PATENT DOCUMENTS

| | | | |
|---|---|---|---|
| 2007/0009578 A1* | 1/2007 | Moller | A61L 15/28 424/443 |
| 2013/0084323 A1 | 4/2013 | Riebman et al. | |
| 2013/0094323 A1 | 4/2013 | Engel | |

FOREIGN PATENT DOCUMENTS

| | | | |
|---|---|---|---|
| WO | 2005062880 | 7/2005 | |
| WO | 2005062896 | 7/2005 | |
| WO | 2010097570 | 9/2010 | |
| WO | WO-2013114132 A1 * | 8/2013 | ........... A61L 15/325 |

OTHER PUBLICATIONS

Hajosch R. et al., "A Novel Gelatin Sponge for Accelerated Hemostatis", Journal of Biomedical Materials Research Part B Applied Biomaterials 2010, John Wiley and Sons Inc. USA, vol. 94, No. 2, Aug. 2010, pp. 372-379.
Search Report—Corresponding PCT Application No. PCT/GB2016/053176, dated Jan. 17, 2017, 4 pages.
Search Report—Corresponding Great Britain Application No. 1518182.9, dated Jun. 20, 2016, 6 pages.
Pogorielov, M.; et al., Abstract of "Haemostatic chitosan coated gauze: in vitro interaction with human blood and in-vivo effectiveness," Biomater Res., 19:22, Published online Nov. 2, 2015, 1 page.
Gupta, B.S.; et al., Excerpt of "Textile materials and structures for wound care products," Science Direct, Advanced Textiles for Wound Care, 2009, 1 Page.
"Gelfoam—absorbable gelatin sponge, USP," [online] retrieved Jul. 2019, from: http://labeling.pfizer.com/ShowLabeling.aspx?id=624, Jul. 2019, 7 Pages.
"Chitosan and Emergency Hemostats," [online] retrieved from: medial hemostat.blogspot.com/2008/02/chitosan-and-emergency-hemostats.html, Feb. 26, 2008, 1 page.
Simo, et al., "Hemostatic Agents in Hepatobiliary and Pancreas Surgery: A Review of the Literature and Critical Evaluation of a Novel Carrier-Bound Fibrin Sealant (TachoSil)", International Scholarly Research Network; ISRN Surgery, vol. 2012, Jan. 1, 2012, pp. 1-12.
Office Action issued on corresponding European Application No. 16784251.7, dated Mar. 4, 2020, 5 pages.
Office Action issued on corresponding European Application No. 16784251.7, dated Mar. 23, 2020, 6 pages.

\* cited by examiner

Figure 6
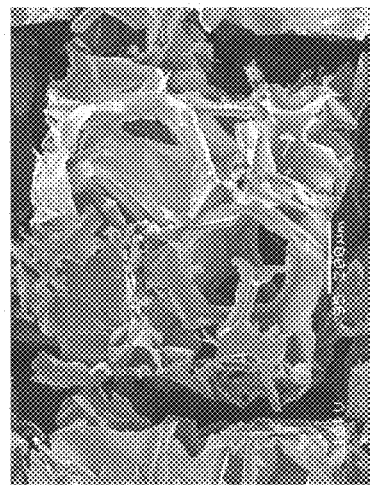
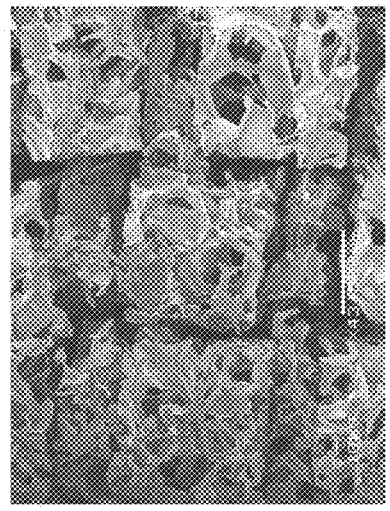
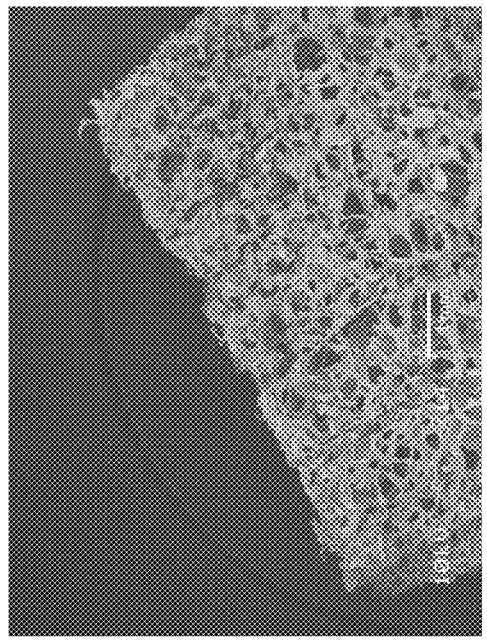
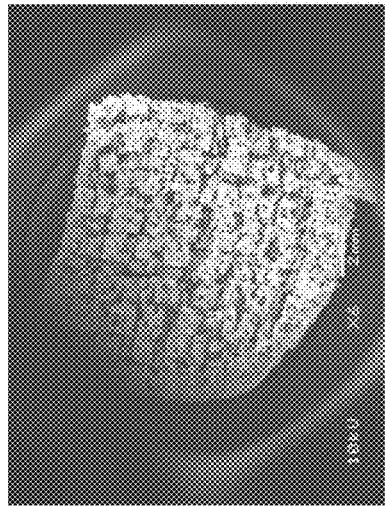

*Figure 7*
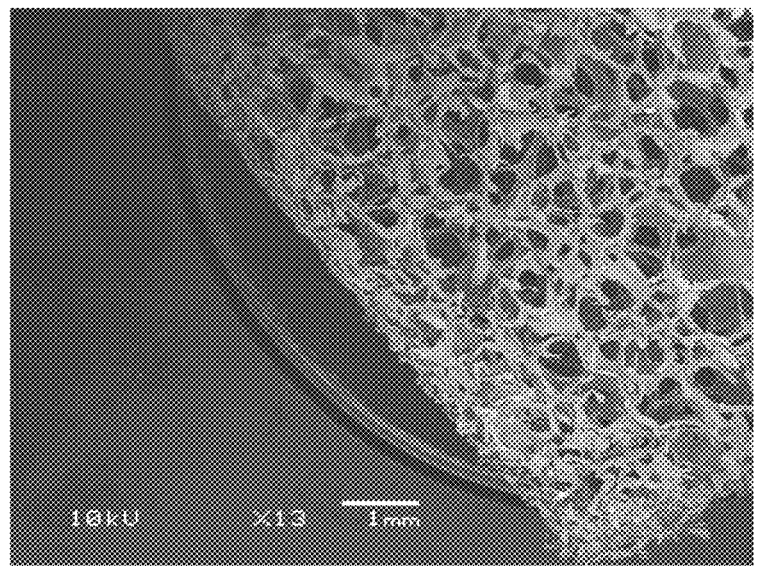
*Figure 8*
(a)  (b)
 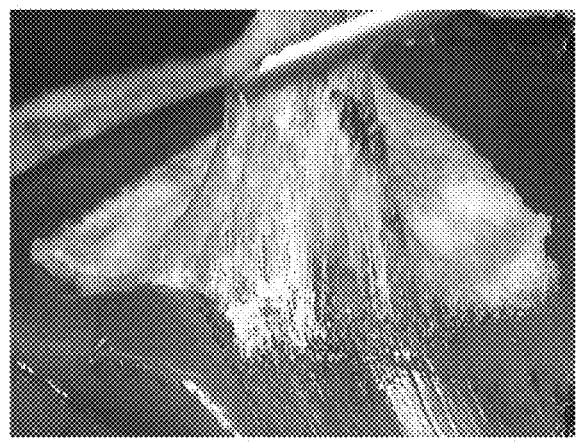

Figure 9
(a)
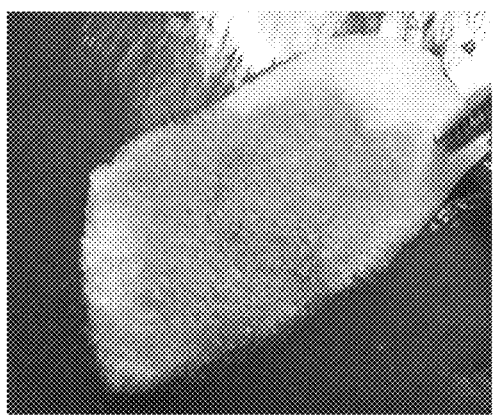
(b)
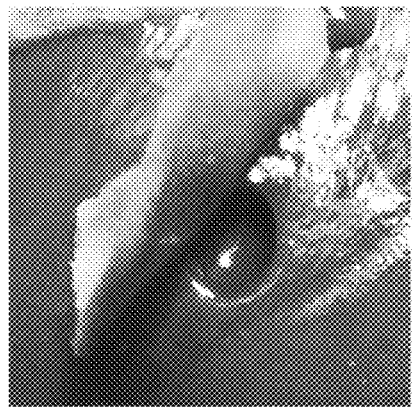
Figure 10
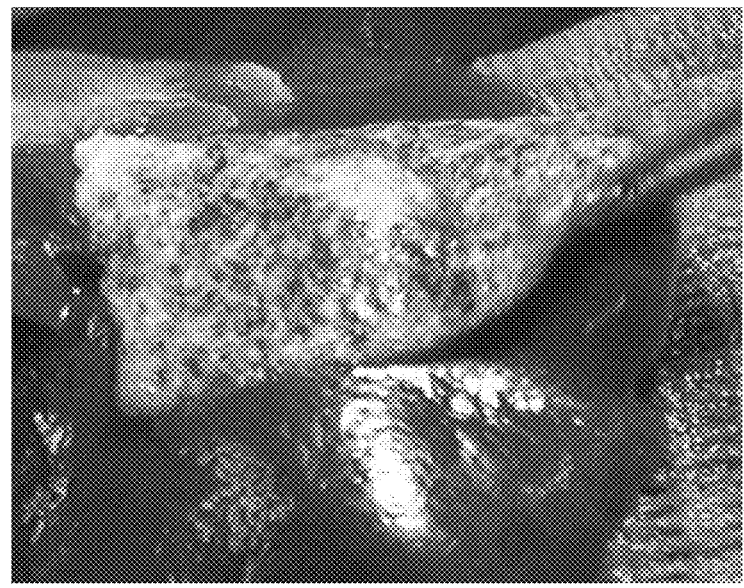

*Figure 15*
(a)
(b)
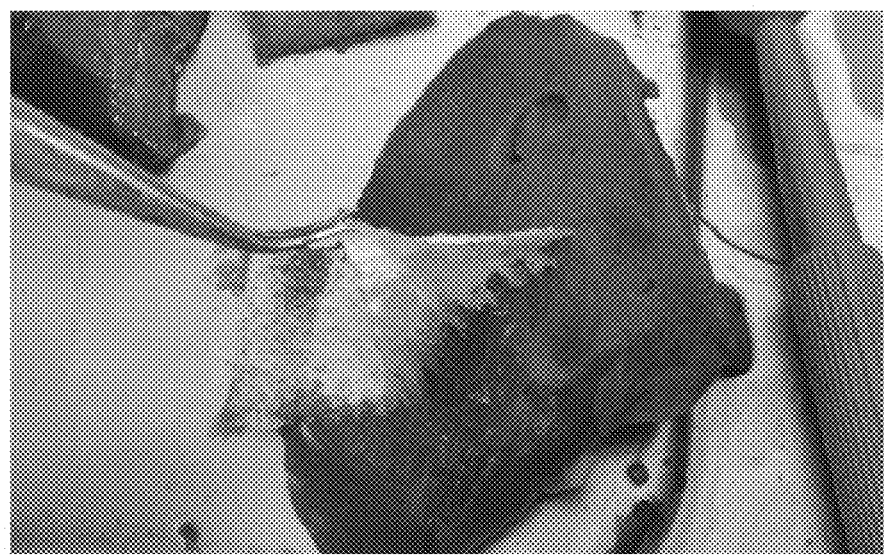

*Figure 16*
(a) 
 (b)

Figure 17
(a) 
(b) 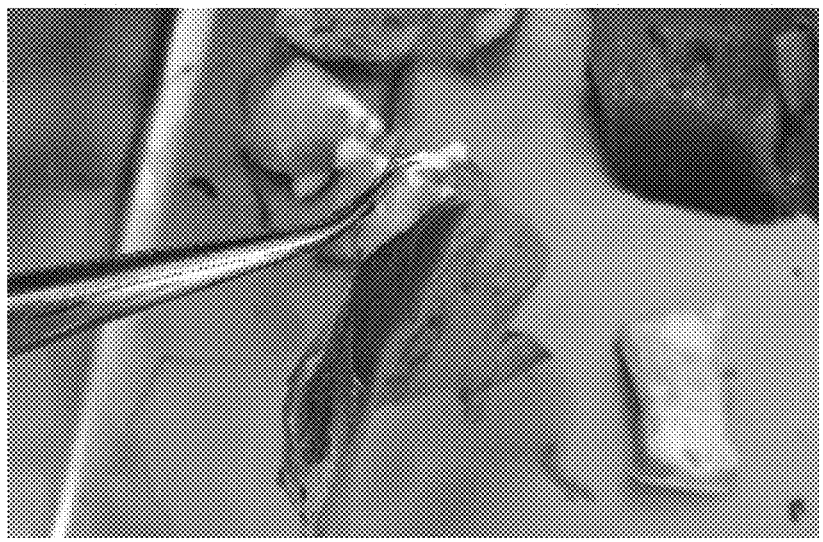

Figure 18
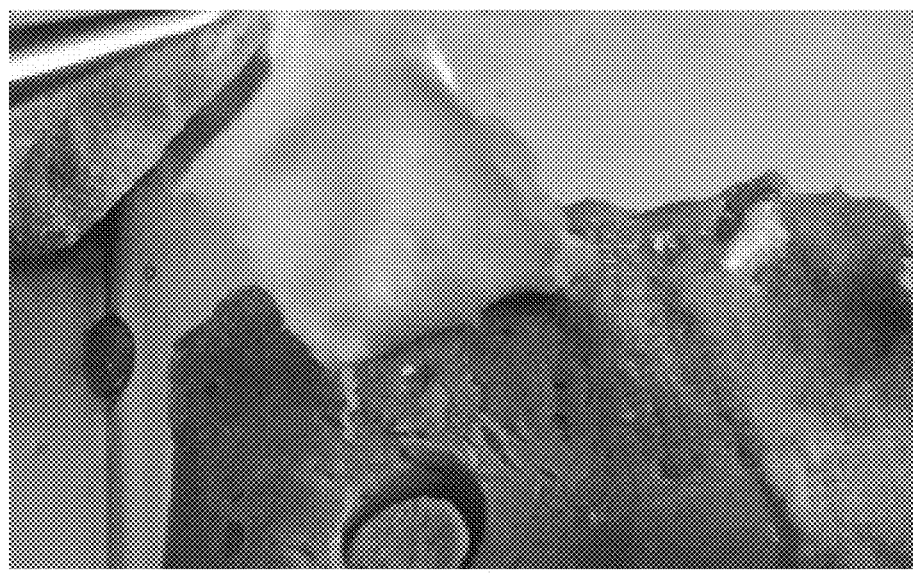
(a)
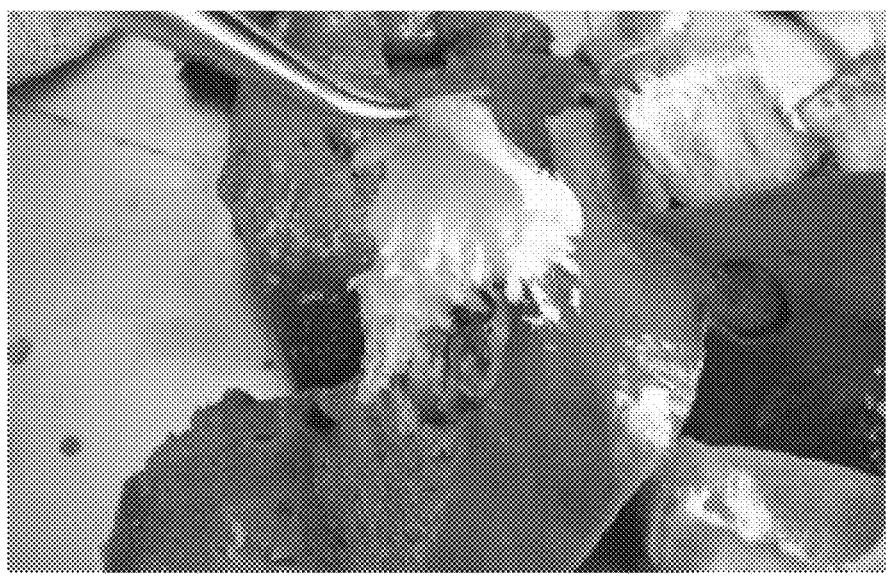
(b)

HAEMOSTATIC DEVICE

This invention relates to haemostatic devices, particularly haemostatic sponges, methods for making such sponges and their uses.

BACKGROUND TO THE INVENTION

Foam sponges manufactured from materials such as gelatin or collagen are commonly used to control bleeding which occurs during surgery. These products range in size, typically from 10 mm×10 mm up to 80 mm×120 mm, with a thickness ranging typically from 2 mm to 10 mm. They are made from bioresorbable materials so they can be left in situ in, or on, the body. Commercially available products include Surgifoam (Ethicon), Gelfoam (Pfizer), Ultrafoam (Bard-Davol) and GelitaSpon (Gelita).

Foam sponges control bleeding by providing a porous matrix that adsorbs blood, and provides a surface that promotes clotting. Clotting factors may also be concentrated as the matrix of the sponge absorbs fluid. These products are reasonably effective and widely used in surgery. They may be used dry, or wetted with saline, or to increase efficacy they may be wetted with a solution of the coagulating enzyme, thrombin or other coagulating agents.

There are certain types of surgery where greater adhesion of the product to the tissue or organ is desirable to ensure it stays in place. Surgical procedures, such as open liver resections, where the sponge is not held in place by surrounding tissue, is one such example. In addition, where a sponge is applied to a partially dry wound or a lightly bleeding wound, there may be insufficient blood clotting to adhere the sponge to the wound.

To address both these concerns, products have been developed in which thrombin and the fibrinogen are dried on the sponge. When such products are applied to a wound the agents dissolve, react and form an adhesive film. The film effectively adheres the product to tissues or organs. An example of such a product is Tachosil (Takeda). Another approach has been to coat synthetic chemicals onto the product to chemically bond it to tissue via a reactive group (e.g. Hemopatch, Baxter). However, a major disadvantage of such products is the associated cost. For example, these products can cost between three and fifteen times the price of regular sponges. Another disadvantage is the risk of exposure of the patient to unidentified blood contaminants, particularly in the case of products with blood-derived thrombin and fibrinogen.

SUMMARY OF THE INVENTION

According to the invention there is provided a bioresorbable haemostatic sponge, the sponge having a tissue-contacting surface divided into a plurality of closely-spaced tissue-contacting elements.

Surprisingly, the applicant has found that haemostatic sponges of the invention may significantly improve adhesion to wounds compared to conventional haemostatic sponges. Furthermore, the improved adhesion can be achieved without having to incorporate expensive coagulants, or reactive chemicals. Also, the applicant has found that haemostatic sponges of the invention may adhere readily to partially dry, or lightly bleeding wounds.

Without wishing to be bound by theory, it is believed that the increased adhesion of the sponge to the wound could be due to a number of factors. For example, the division of the tissue-contacting surface into discrete tissue-contacting elements may increase the surface area of the sponge in contact with the wound. Conventional foam sponges may not adhere well to tissue because of a poor surface contact. The porous nature of the material may mean that only a limited amount of the material actually contacts the wound surface, leading to poor adhesion.

Alternatively, or additionally, the tissue-contacting elements on the tissue-contacting surface may allow the sponge to more readily conform to the topography of a wound, thus increasing surface contact with the wound. Conventional sponges, which have continuous surfaces, may not be able to conform to the wound in the same manner.

Furthermore, the presence of individual tissue-contacting elements which may move independently of one another, may make the sponge more resistant to forces acting to displace the sponge. Lifting one edge, for example, may raise a proportion of the tissue-contacting elements from the wound surface whilst the rest remain in contact with the wound. A conventional sponge with a continuous surface, may not provide this benefit. A force (such as a shear force) applied at one edge of a conventional sponge may be more effectively transmitted across the sponge and result in displacement. The tissue-contacting elements of sponges of the present invention may increase friction between the sponge and the wound surface and resist lateral displacement of the sponge.

Furthermore, the channels created between the tissue-contacting elements may allow wound exudate to have more rapid access to the sponge thereby accelerating the adhesion process and, depending on the dimensions of the channel, potentially also creating a capillary effect through the sponge.

As a bioresorbable haemostatic sponge, the sponge according to the invention is particularly advantageous as the sponge may be used on internal wounds, for example during surgery. Increased adherence of the sponge to the tissue of the wound is particularly advantageous in such an application as the sponge can then be applied to the desired tissue surface and remain in place without the need for any additional adhering means. The sponge can therefore be left inside the patient's body after surgery where it will be bioresorbed over time, ie broken down and absorbed by the body, without need for mechanical removal.

The bioresorbable haemostatic sponge is preferably for use on wounds excluding skin wounds and skin ulcers and is most preferably suitable for use on internal wounds.

A bioresorbable material is a material that can be broken down and resorbed by the body and that does not require mechanical removal.

In preferred embodiments, the sponge has a base portion which is undivided and from which the tissue-contacting elements extend. The tissue-contacting elements may therefore be regarded as projections from the undivided base portion. For example, each tissue-contacting element may comprise a first end (or base end) which is connected or joined to the undivided base portion, and a second end (or face) which is not connected or joined to the base portion. Thus, the second faces form the tissue-contacting surface of the sponge. In other words, the base portion may provide a common body from which each tissue-contacting element, projects. The base portion may permit effective absorption of bodily fluids. The tissue-contacting surface may also be referred to as a wound-contacting surface.

The sponge according to the invention may have any suitable shape, but will most commonly be cuboidal, with a length and width that are substantially greater than its thickness. Thus, the sponge will typically be generally square or rectangular, with a length and width of from about 1 cm to about 30 cm or more, more commonly between about 2 cm and about 10 cm, and a thickness of from about 2 mm to about 20 mm, more commonly from about 5 mm to about 15 mm.

The sponge of the invention may have the form of a cuboidal block of material that is, at least prior to use and absorption of fluid, quite rigid. In other embodiments, particularly those in which the sponge is relatively thin, the sponge may have the form of a flexible sheet or pad.

Although the sponge will most commonly be square or rectangular in shape, other shapes are possible, e.g. circular or hexagonal. The sponge may also be supplied in the form of an oversized sheet, from which suitably sized and shaped pieces may be cut to suit the needs of a particular procedure.

The base portion and the tissue-contacting surface of the sponge are preferably both formed from the same sponge material. Thus, the sponge may comprise a unitary construct in which the base portion and tissue-contacting elements are formed integrally. Advantageously, the sponge may be easy to manufacture because in some embodiments, the tissue-contacting elements are formed by making modifications to a surface of a sponge identical to a pre-existing, commercially-available haemostatic sponge, or by making minor adjustments to the methods used to manufacture such sponges.

Each tissue-contacting element may project in a substantially perpendicular orientation relative to the base portion. FIG. 1, for instance, shows an embodiment in which each tissue-contacting element projects in a substantially perpendicular orientation relative to the base portion.

The tissue-contacting elements will in many cases be formed on only one major face of the sponge, the other face being undivided (and hence having a surface like that of a conventional haemostatic sponge). In such cases, the divided face of the sponge may be applied to the tissue where it is desired for there to be good adhesion between the sponge and tissue, or the undivided face may be applied if less adhesion is for any reason desirable.

In other embodiments, however, both major faces of the sponge may be divided into tissue-contacting elements, so that both faces comprise projections and both faces exhibit improved adhesion to tissue. Such embodiments may be particularly useful where the sponge is interposed between two tissue surfaces and the sponge should adhere to both, or simply because with such embodiments the user does not need to choose which surface to apply and so the risk of mis-application is reduced.

Where only one face of the sponge is divided into tissue-contacting elements, that face, or more commonly the opposite face of the sponge, may carry a visual indication so that a user can readily distinguish the faces. For instance, the surface may be printed with an image or alphanumeric marking using an appropriate bioresorbable chromophore, for example methylene blue.

The tissue-contacting elements may take a number of different forms. For example, the tissue-contacting elements may be finger-like or columnar. In other embodiments, the tissue-contacting elements may be in the form of ridges or corrugations.

Preferably, each tissue-contacting element is of a particular size and shape that enables it to bend, flex, tilt or fold independently of other tissue-contacting elements. For example, each tissue-contacting element may be able to deviate from an orientation that is substantially perpendicular (i.e. 90°) to the base portion. Each tissue-contacting element may be able to vary the angle of its longitudinal axis relative to the base portion. Each tissue-contacting element may be able to move such that it lies flat on the base portion, or parallel to the base portion (e.g. 0° relative to the base portion). Independent bending, flexing, tilting or folding of each tissue-contacting element may be facilitated if each tissue-contacting element is finger-like or columnar. The plurality of tissue-contacting elements may thus form a brush-like surface on the sponge.

FIG. 1 shows a schematic diagram of an embodiment of the invention which exemplifies particular dimensions referred to herein. This includes depth (or thickness or height) of the sponge, depth (or height or length) of the tissue-contacting elements, width of the sponge and length of the sponge.

In some embodiments, each tissue-contacting element has a depth of at least 0.1 mm. In some embodiments, each tissue-contacting element has a depth of at least 0.5 mm. In some embodiments, each tissue-contacting element has a depth of at least 1 mm. In some embodiments, each tissue-contacting element has a depth of at least 2 mm.

In some embodiments, each tissue-contacting element has a depth of 10 mm or less. In some embodiments, each tissue-contacting element has a depth of 8 mm or less. In some embodiments, each tissue-contacting element has a depth of 5 mm or less.

In some embodiments, each tissue-contacting element has a depth of 0.1 to 10 mm, 0.5 to 10 mm, 1 to 10 mm or 2 to 10 mm. In some embodiments, each projection has a depth of 1 to 10 mm. In some embodiments each tissue-contacting element has a depth of 1 to 8 mm or 1 to 5 mm.

However, it will be appreciated that the depth of the tissue-contacting elements may depend on the dimensions of the sponge. For example, if the depth of the sponge is shallow (i.e. the sponge is thin), longer tissue-contacting elements may be undesirable as this may affect the structural integrity of the sponge. In some circumstances, longer tissue-contacting elements may provide greater adhesion to a wound. However, longer tissue-contacting elements, relative to the depth of the sponge, could compromise the haemostatic efficacy of the sponge.

In some embodiments, the depth of each tissue-contacting element is 80% or less of the depth of the sponge. In some embodiments, the depth of each tissue-contacting element is 60% or less of the depth of the sponge. In some embodiments, the depth of each tissue-contacting element is 50% or less of the depth of the sponge. In some embodiments, the depth of each tissue-contacting element is 35% or less of the depth of the sponge.

A variety of cross-sectional shapes may be suitable for the tissue-contacting elements. For example, the cross-sectional shape of each tissue-contacting element may be substantially rectangular or triangular. The tissue-contacting elements may alternatively have irregular cross-sectional shapes.

The second end (or face) of each tissue-contacting element is generally substantially flat or planar. This shape may be readily obtained if projections are formed by cutting or incising a surface of the sponge (see below).

In particularly preferred embodiments, the cross-sectional area of each tissue-contacting element is 50 mm$^2$ or less, 25 mm$^2$ or less, 10 mm$^2$ or less, or 5 mm$^2$ or less. The cross-sectional area is preferably less than 10 mm$^2$.

The cross-sectional area of each tissue-contacting element may be greater than or equal to 0.05 mm$^2$, greater than or equal to 0.1 mm$^2$, greater than or equal to 0.5 mm$^2$, or greater than or equal to 1 mm$^2$.

The cross-sectional area of each tissue-contacting element may be between 0.05 mm$^2$ and 25 mm$^2$. Preferably, the cross-sectional area of each tissue-contacting element is 0.25 mm$^2$ to 5 mm$^2$.

In preferred embodiments, the cross-sectional area of each tissue-contacting element is substantially uniform, i.e. the cross-sectional area is consistent throughout the depth of the tissue-contacting element. However, in some embodiments, the projections may not have a substantially uniform cross-section. The cross-sectional area generally refers to the area of the second end (or face) of the tissue-contacting element.

The maximum cross-sectional linear dimension of each tissue-contacting element may be 20 mm or less, 10 mm or less, or 6 mm or less. The maximum cross-sectional linear dimension of each tissue-contacting element may be 0.2 mm or greater, 0.5 mm or greater or 1 mm or greater. For example, the maximum cross sectional linear dimension of each tissue-contacting element may be 0.2 to 20 mm, or 0.5 to 10 mm. If a tissue-contacting element has a uniform rectangular cross-section, for instance, the maximum cross-sectional linear dimension would be the linear dimension between opposing vertices. If the tissue-contacting element does not have a substantially uniform cross-section (e.g. it is wider at one end than another), the maximum cross-sectional dimension would be the part along the depth of the tissue-contacting element that has the largest linear dimension (e.g. at the widest part of the projection).

Although smaller tissue-contacting elements (e.g. tissue-contacting elements with a smaller cross-sectional area) may lead to stronger adhesion in some circumstances, there may be a limit to how small the tissue-contacting elements can be. For example, the tissue-contacting element size may be limited by the pore size of the sponge. Very small tissue-contacting elements may be difficult to create in some types of foam materials.

Bending, flexing, tilting or folding of the tissue-contacting elements independently of other tissue-contacting elements may be hindered if, for example, the cross-sectional area (e.g. maximum cross-sectional area) or maximum cross-sectional linear dimension is large relative to the depth of the tissue-contacting element. For instance, shallow tissue-contacting elements with a large maximum cross-sectional area or large cross-sectional linear dimensions may not be able to bend independently of other tissue-contacting elements. Consequently, in most embodiments, the maximum cross-sectional linear dimension of each tissue-contacting element is no more than ten times the depth of the tissue-contacting element. In more preferred embodiments, the maximum cross-sectional linear dimension of each tissue-contacting element is no more than five times the depth of the tissue-contacting element. In even more preferred embodiments, the depth of each projection may be greater than or equal to its maximum cross-sectional linear dimension. The maximum cross-sectional linear dimension of each tissue-contacting element may be at least five times less than the depth of the tissue-contacting element or at least ten times less than the depth of the tissue-contacting element.

Preferably, the cross-sectional linear dimension at the base end (or first end) of each tissue-contacting element is not substantially greater than the cross-sectional linear dimension at the face (or second end). For example, it is preferable that the projections are not substantially dome-shaped, cone-shaped, pyramid-shaped or pillow-shaped. Such shapes may make it difficult for projections to bend independently of other projections. In general, it is preferred that the cross-sectional linear dimension at the base of each projection is no more than two times or less than the cross-sectional linear dimension at the face.

The number and/or size of the tissue-contacting elements could be varied in order to adjust the adhesive capability of the sponge. For example, dividing the tissue-contacting surface into a large number of tissue-contacting elements, each with a small cross-sectional area (such as shown in the embodiments of FIGS. 1, 2 and 3) may result in a very strong adhesion. As a general rule, improved adhesion is preferable. However, different surgical situations may require different adhesive capabilities. For some applications, it may be desirable to use a sponge with a weaker adhesive capability. This may be the case if there is a desire to remove the sponge from the wound after a limited period of time. If the adhesion is too strong, it may make the sponge difficult to remove, which could cause damage to tissue. Dividing the tissue-contacting surface into only a small number of tissue-contacting elements with larger cross-sectional areas may result in a slight improvement in adhesion compared to conventional haemostatic sponges, but may still be readily removed. The skilled person can select a particular, size, shape and arrangement of tissue-contacting elements that leads to a desirable level of adhesion, by comparing to a continuous haemostatic sponge with an unmodified surface. A suitable method for testing various sizes, shapes and arrangements of tissue-contacting elements is described in the Examples. Example 4, for instance, describes an in vitro method that could be used to readily test permutations of tissue-contacting elements, and permit optimisation of adhesion.

In some embodiments, the tissue-contacting elements form an array. For example, the tissue-contacting elements may be in an ordered arrangement such as in distinct columns and/or rows. Each tissue-contacting element comprised in the tissue-contacting surface may have substantially the same cross-sectional shape, and/or each tissue-contacting element may have substantially the same cross-sectional area.

The tissue-contacting elements are closely-spaced together. By closely spaced is meant that the tissue-contacting elements are arranged so that each tissue-contacting element is within at least 5 mm of another tissue-contacting element. Preferably, each tissue-contacting element is within 1 mm of another tissue-contacting element, most preferably within 0.5 mm of another tissue-contacting element.

The tissue-contacting elements are preferably formed by cutting an existing bioresorbable haemostatic sponge. The space between tissue-contacting elements is then generally determined by the width of the cutting means. The width of the cutting means is preferably between 0.05 mm and 0.5 mm.

The tissue-contacting surface may be divided such that there are at least 4 tissue-contacting elements per 100 mm$^2$ of the tissue contacting surface, preferably at least 10 tissue-contacting elements per 100 mm$^2$ of the tissue-contacting surface, and most preferably at least 25 tissue-contacting elements per 100 mm$^2$ of the tissue-contacting surface.

The sponge may have a variety of dimensions, which may depend on its intended application. Typically, the length of the sponge is about 150 mm or less. Typically, the width of the sponge is about 50 mm or less. The sponge may have a length of 10 mm or greater, and/or a width of 10 mm or greater. For example, the length may be 10 to 150 mm. The width may be 10 to 50 mm. Typically the depth (or thickness) of the sponge is about 10 mm or less. The depth of the sponge may be from 0.2 to 10 mm.

The sponge is a foam. Preferably it is an open-cell foam. It may thus provide a porous matrix suitable for absorbing and/or adsorbing bodily fluids, such as blood or wound exudate. Suitable materials for the sponge are known in the art and include gelatin, collagen, starch and hyaluronic acid. Commercially-available sponge materials suitable for use in the invention include, for example, Surgifoam (Ethicon), Gelfoam (Pfizer), Ultrafoam (Bard-Davol) and GelitaSpon (Gelita). Foam sponges of the invention are distinguished from fibrous or fabric-based haemostats which utilise woven or non-woven fibres (e.g. felt-like haemostats). Preferably the sponge is a gelatin or collagen sponge.

Foam sponges are typically manufactured by foaming a solution comprising a sponge-forming material (e.g. gelatin), and then drying the foam. Drying may be achieved by baking or lyophilisation. Gelatin, for instance, may be cross-linked in order to prevent it from dissolving in the blood too readily (because gelatin is soluble in temperatures above 30° C.). Cross-linking may be achieved with a chemical cross-linking agent such as formaldehyde, glutaraldehyde and carbodiimides, or by treatment of the sponge with dry heat (e.g. 100-160° C. for several hours).

A suitable pore size may be selected depending on the intended role of the sponge, for example the type of tissue to which the sponge is to be brought into contact or the type of bodily fluid that the sponge is intended to absorb. Typically, the sponge has pores with a diameter of 3 mm or less. For instance, at least 50%, at least 60%, at least 70%, at least 80%, at least 90% or at least 65% of the pores may have a diameter of between 1 and 1500 µm or between 5 and 1000 µm, more preferably between 5 and 750 µm.

Preferably, the haemostatic sponge is sterile. The sponge may be sterilised by heating. Prior to use, the sponge may be kept in packaging, such as air-tight packaging, to maintains sterility.

The haemostatic sponge is preferably manufactured by making a series of incisions into a surface of an otherwise conventional sponge. For example, a blade (with a width of, for example, 0.1 mm to 0.3 mm) may be used to cut or score a surface of a sponge and divide the surface of the sponge into a plurality of closely-spaced tissue contacting elements.

Thus, besides the incisions made in the surface of the sponge, the sponge is essentially the same as a conventional haemostatic sponge and would be expected to have similar physical properties, apart from the surprising increased adherence of the modified sponge to a wound surface. For example, on contact with liquid a conventional gelatin haemostatic sponge reduces in volume slightly before subsequently recovering substantially all of its original volume on absorption of liquid. A gelatin sponge modified according to the invention has been found to behave in a similar manner.

In some embodiments, periodic parallel and straight cuts may be made both along the width of the surface of the sponge and along the length of the surface of the sponge. This may create an array of tissue-contacting elements on the surface of the sponge, each of which has substantially the same cross-sectional shape and cross-sectional area. Varying the cutting positions will allow the number, cross-sectional area and shape of the tissue-contacting elements to be varied.

It is also envisaged that the surface of the sponge could be divided into tissue-contacting elements by using a pre-fabricated cutting or embossing tool (such as the tool shown in FIG. 18) such that all incisions could be made simultaneously. Alternative cutting technologies that could be employed include rotating blades or lasers.

Consequently, according to the invention, there is provided a method comprising cutting, incising or embossing a surface of a bioresorbable haemostatic sponge to form a haemostatic sponge comprising a tissue-contacting surface divided into a plurality of closely-spaced tissue-contacting elements.

The tissue-contacting surface could also be divided into closely-packed tissue-contacting elements by a moulding process during the manufacture of the sponge.

According to the invention, there is provided a method of controlling bleeding or promoting blood clotting, comprising administering a haemostatic sponge of the invention, to a wound.

According to the invention there is provided a haemostatic sponge according to the invention, for use in controlling bleeding or promoting blood clotting.

According to the invention there is provided use of a sponge according to the invention for the manufacture of a medicament for use in controlling bleeding or promoting blood clotting.

In some embodiments, agents may be added to, or immobilised to, the sponge which assist adhesion of the sponge to a wound site. The agent may be a haemostatic agent. For example, such agents may be immobilised to the tissue-contacting surface of the sponge. Such agents may be adhered on to the sponge by non-covalent immobilisation (such as by drying) or by covalently immobilising the agents to the sponge.

In some embodiments, the haemostatic agents may comprise coagulants, or clotting factors such as thrombin and/or fibrinogen. Alternatively, the agents may comprise reactive groups, which enable chemical bonds to be formed with tissue, on contact. For example, Hemopatch (Baxter) incorporates NHS-PEG groups which enable tissue attachment.

In some embodiments, the haemostatic agents may comprise carriers with a plurality of fibrinogen binding peptides immobilised to each carrier. Examples of such agents are described in WO2005/035002; WO2007/015107; WO2008/065388; WO2012/104638; WO 2013/114132; and WO2015/104544, of which the contents of each is incorporated herein by reference. WO 2012/104638 describes how such haemostatic agents may be immobilised to gelatin. In one embodiment the fibrinogen binding peptide may comprise the sequence G(P,H)RX, wherein P,H means that either proline or histidine is present in that position and X refers to any amino acid. The carrier may be soluble or insoluble but is preferably soluble. The sequence may be present at the amino-terminal end of the fibrinogen binding peptide, e.g. $NH_2$-G(P,H)RX—. The fibrinogen-binding peptide may be 4-50 amino acids in length, preferably 4-10 amino acids in length. The fibrinogen binding peptide may be spaced from the carrier by a spacer, which may be a peptide spacer, or a non-peptide spacer such as polyethylene glycol. Preferably, the agent forms a biogel when contacted by fibrinogen. Each fibrinogen molecule may bind at least two of the fibrinogen binding peptides, resulting in formation of a biogel in which the fibrinogen molecules are linked together via the carriers by non-covalent bonds between the fibrinogen molecules and the fibrinogen binding peptides. The carrier may be an albumin carrier.

In some embodiments, the agent may be a peptide conjugate such as a peptide dendrimer. A dendrimer may comprise a branched core and a plurality of fibrinogen-binding peptides separately covalently attached to the branched core. The branched core may comprise one or more multifunctional amino acids (e.g. tri- or tetra-functional amino acids). Each multifunctional amino acid, or a plurality of multifunctional amino acids, may have one or more fibrinogen binding peptides covalently attached to it.

Examples of suitable conjugates and dendrimers are described in WO2015/104544. For example, a peptide dendrimer may comprise the following general formula:

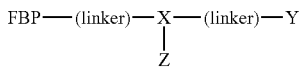

where:
FBP is a fibrinogen-binding peptide;
-(linker)- is an optional linker, preferably a non-peptide linker;
X is a tri-functional amino acid residue, preferably lysine, ornithine, or arginine;
Y is —FBP, or —NH$_2$;
Z is -(linker)-FBP when Y is —FBP, or -[—X$_n$-(linker)-FBP]$_a$-(linker)-FBP when Y is —NH$_2$;
where:
X$_n$ is a tri-functional amino acid residue, preferably lysine, L-ornithine, or arginine; and
a is 1-10, preferably 1-3.

For example, when Y is NH$_2$, Z is -[—X$_n$-(linker)-FBP]$_a$-(linker)-FBP, the structure of the dendrimer is as follows:
where a is 1:

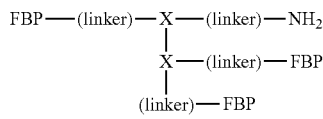

or, where a is 2:

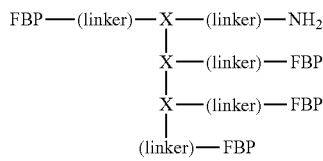

or, where a is 3:

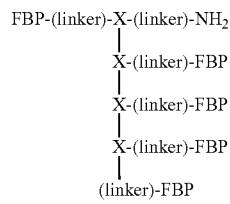

Alternatively, Z is -[—X$_n$-(linker)-FBP]$_a$-(linker)-FBP when Y is —FBP;
where:
X$_n$ is a tri-functional amino acid residue, preferably lysine, L-ornithine, or arginine; and
a is 1-10, preferably 1-3.

For example, when Y is —FBP, Z is -[—X$_n$-(linker)-FBP]$_a$-(linker)-FBP and a is 1, the structure of the dendrimer is as follows:

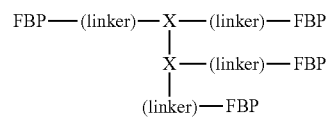

DESCRIPTION OF SPECIFIC EMBODIMENTS OF THE INVENTION

Embodiments of the invention will now be described, by way of example, with reference to the accompanying drawings, in which:

FIGS. 6a to 6d show SEM images of a haemostatic sponge according to an embodiment of the invention;

FIG. 7 shows an SEM image of a commercially-available haemostatic sponge (GelitaSpon, by Gelita);

FIGS. 8a and 8b show the in vivo adhesive properties of a haemostatic sponge according to an embodiment of an invention;

FIGS. 9a and 9b show the in vivo adhesive properties of a commercially-available haemostatic sponge (GelitaSpon, by Gelita);

FIG. 10 shows the in vivo adhesive properties of a commercially-available haemostatic sponge (Tachosil by Taekeda);

FIGS. 15a and 15b show a comparison between the adhesive properties of a haemostatic sponge according to the invention (FIG. 15b), and a commercially-available haemostatic sponge (FIG. 15a) (GelFoam);

FIGS. 16a and 16b show a comparison between the adhesive properties of a haemostatic sponge according to the invention (FIG. 16b), and a commercially-available haemostatic sponge (FIG. 16a) (SpongoStan Standard);

FIGS. 17a and 17b show a comparison between the adhesive properties of a haemostatic sponge according to the invention (FIG. 17b), and a commercially-available haemostatic sponge (FIG. 17a) (KolSpon);

FIGS. 18a and 18b show a comparison between the adhesive properties of a haemostatic sponge according to the invention (FIG. 18b), and a commercially-available haemostatic sponge (FIG. 18a) (UltraFoam);

Figure 1:
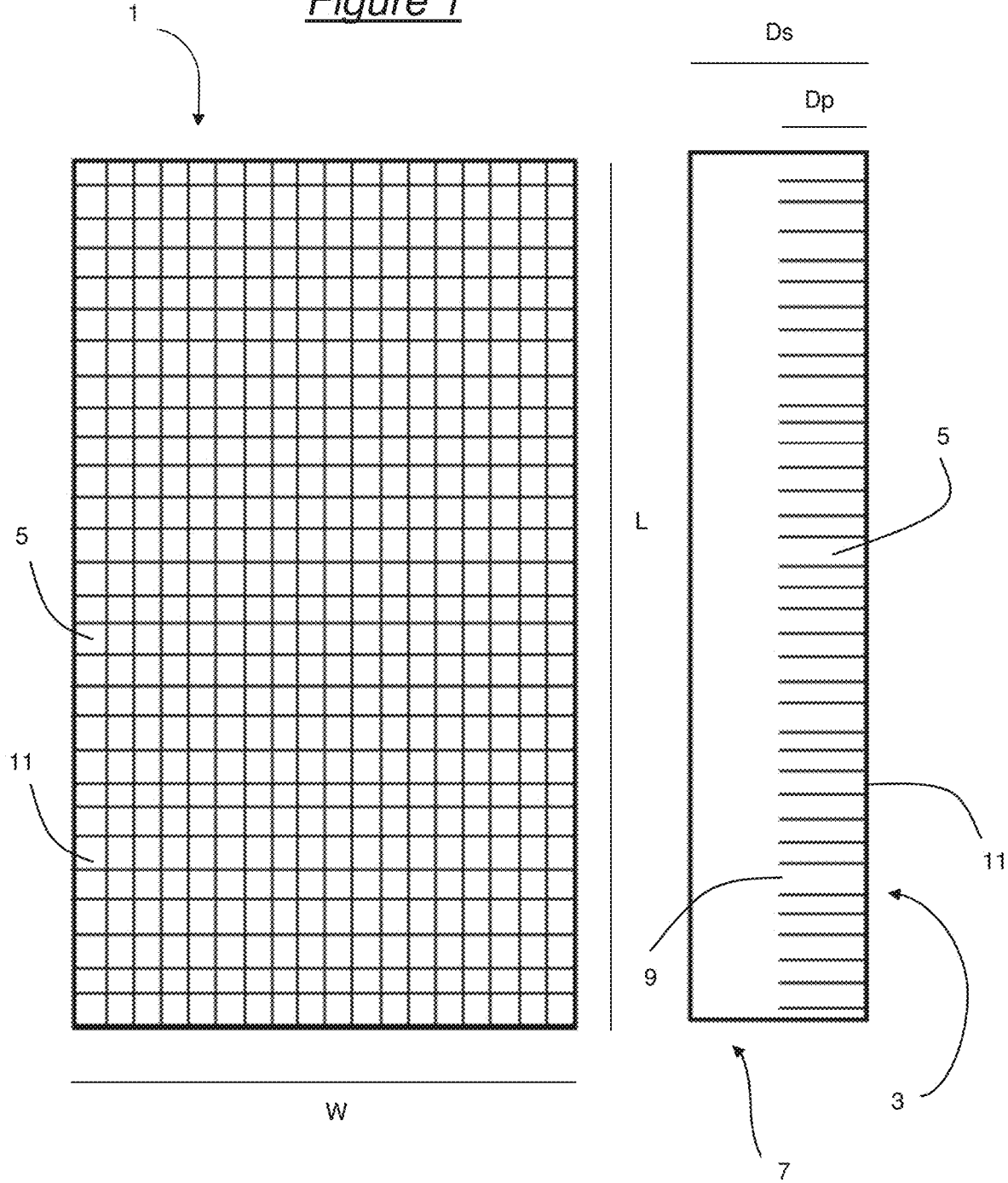
FIG. 1 is a schematic representation (plan view (left) and side view (right)) of a haemostatic sponge according to an embodiment of the invention.

A haemostatic gelatin foam sponge 1 as shown in FIG. 1 has a tissue-contacting surface 3. The tissue-contacting surface is divided into a series of finger-like or columnar tissue-contacting elements 5. The tissue-contacting elements project in a substantially perpendicular orientation from a base portion 7 and each has a rectangular cross-section. Each tissue-contacting element 5 has a first end (or base end) 9 which is attached to the base portion, and a second end (or face) 11, which is furthest from the base portion.

FIG. 1 indicates the length of the sponge (L), width of the sponge (W), depth of the sponge (Ds) and the depth of the tissue-contacting elements (Dp). The depth of the sponge may also be referred to as the height or thickness of the sponge and the depth of tissue-contacting element may also be referred to as the height (or length) of the tissue-contacting element.

The sponge 1 is manufactured by making a series of periodic incisions into the surface of a gelatin foam sponge using a razor blade. A series of incisions are made lengthwise, followed by a series of incisions width-wise, the incisions extending part-way through the sponge.

In use, the sponge 1 is applied to a wound such that the tissue-contacting elements 5 of the tissue-contacting surface 3 are in contact with the wound.

Figure 2:
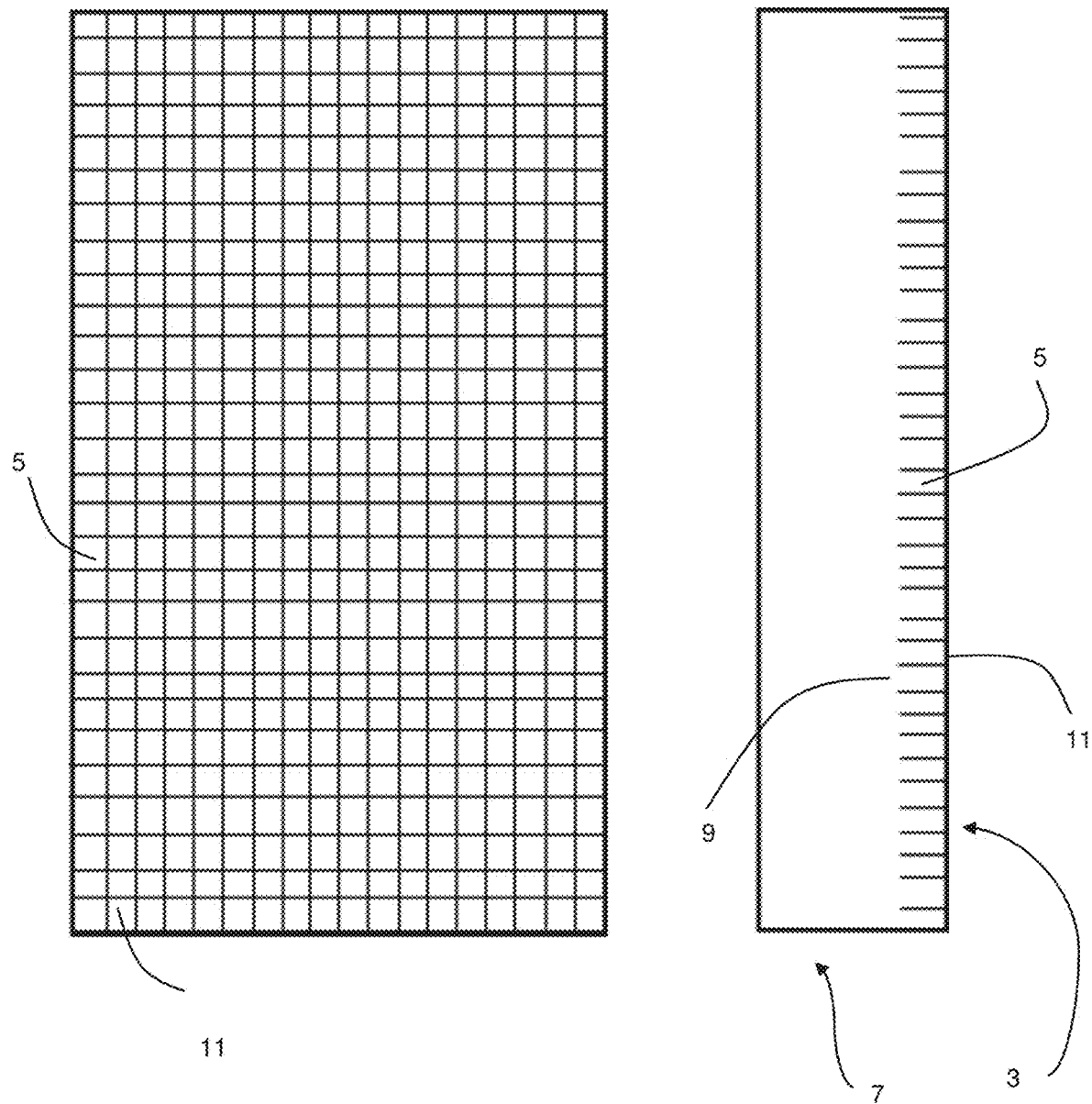
FIG. 2 is a schematic representation (plan view (left) and side view (right)) of a haemostatic sponge according to an embodiment of the invention.

A haemostatic gelatin sponge as shown in FIG. 2, is substantially the same as the haemostatic sponge of FIG. 1, apart from the fact that the incisions are less deep, such that the tissue-contacting elements 5 are shorter. Features similar to those in FIG. 1 have been assigned like reference numerals.

Figure 19:
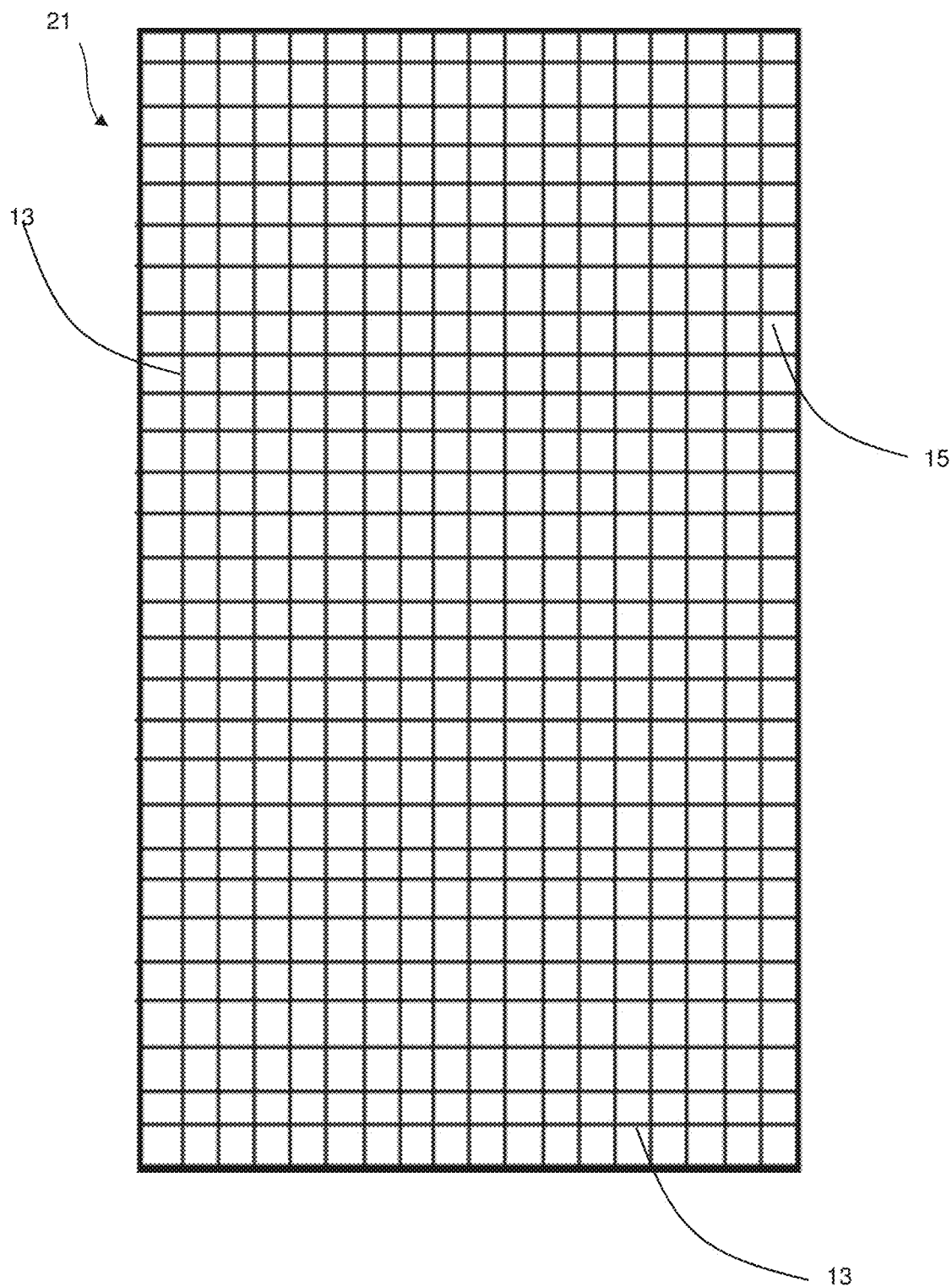
FIG. 19 shows a cutting tool (plan view) that can be used to manufacture a haemostatic sponge according to an embodiment of the invention as shown in FIGS. 1 and 2.
Figure 20:
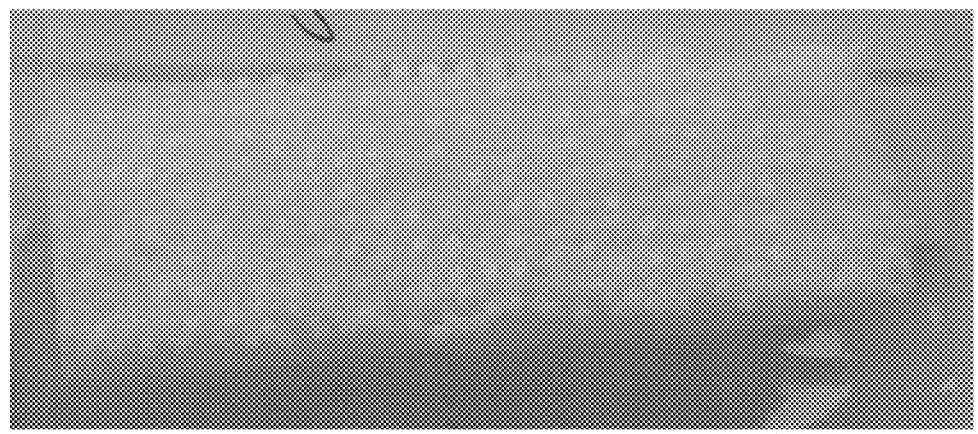
FIG. 20 shows a photograph of a haemostatic sponge according the invention where the tissue-contacting elements have been formed using an automated robotic blade.
Figure 21:
FIG. 21 shows the adhesive properties of the haemostatic sponge of FIG. 20.

FIG. 19 shows a schematic plan view of a cutting tool 21 that could be used to manufacture a haemostatic sponge as shown in FIGS. 1 and 2. The tool has a series of blades 13, arranged length-wise and width-wise, to define an array of substantially rectangular voids 15. The tool can be inserted into the surface of a sponge, so as to make a number of simultaneous cuts, and create projections of a pre-determined cross-sectional area.

Figure 3:
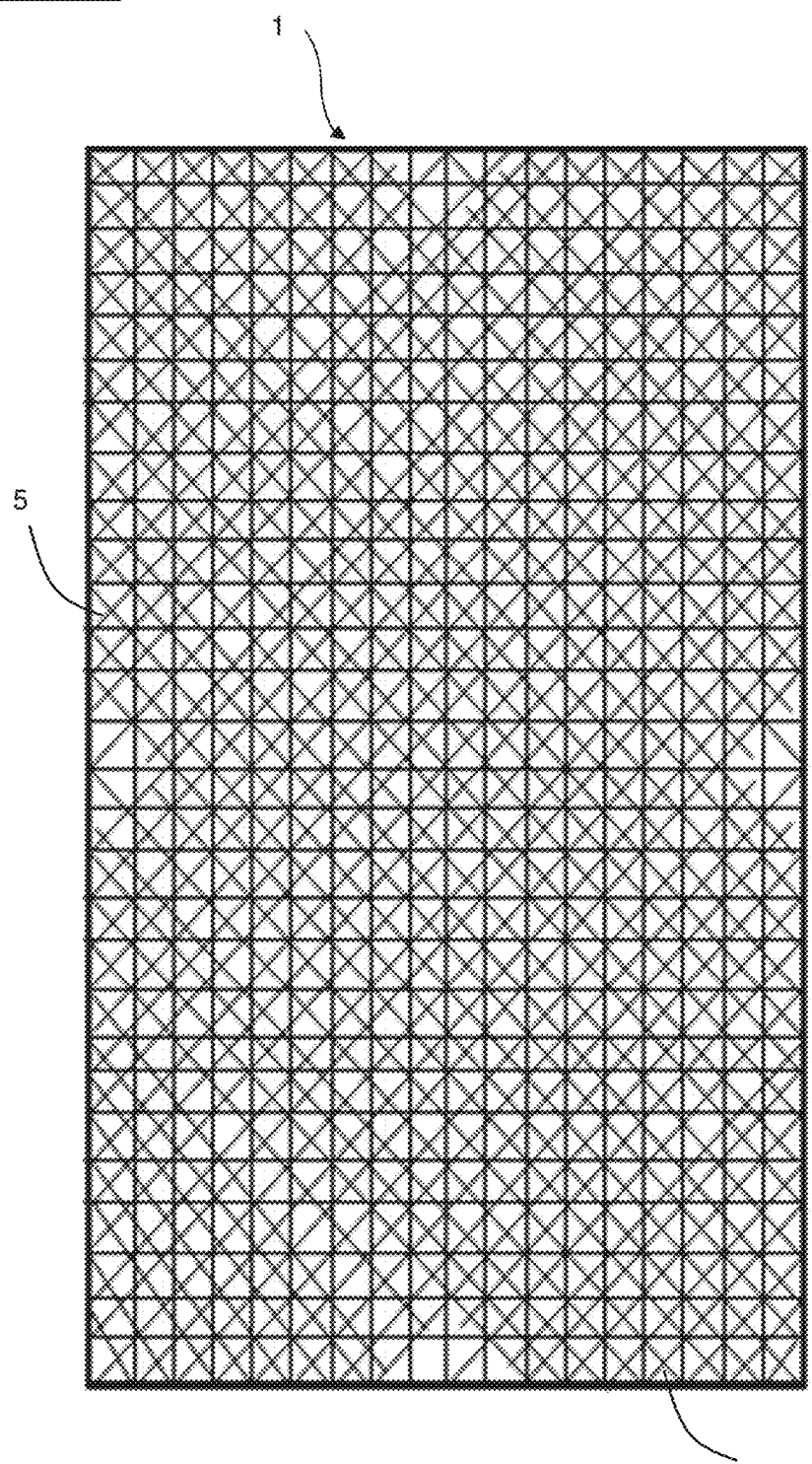
FIG. 3 is a schematic representation (plan view) of a haemostatic sponge according to an embodiment of the invention.

A haemostatic gelatin sponge as shown in FIG. 3, is similar to the haemostatic sponges of FIGS. 1 and 2. Similar features have been assigned like reference numerals. However, further diagonal incisions have been made through each tissue-contacting element to create four times as many tissue-contacting elements, each tissue-contacting element having a triangular cross-section with a surface area of approximately one quarter that of the tissue-contacting elements of FIGS. 1 and 2.

Figure 4:
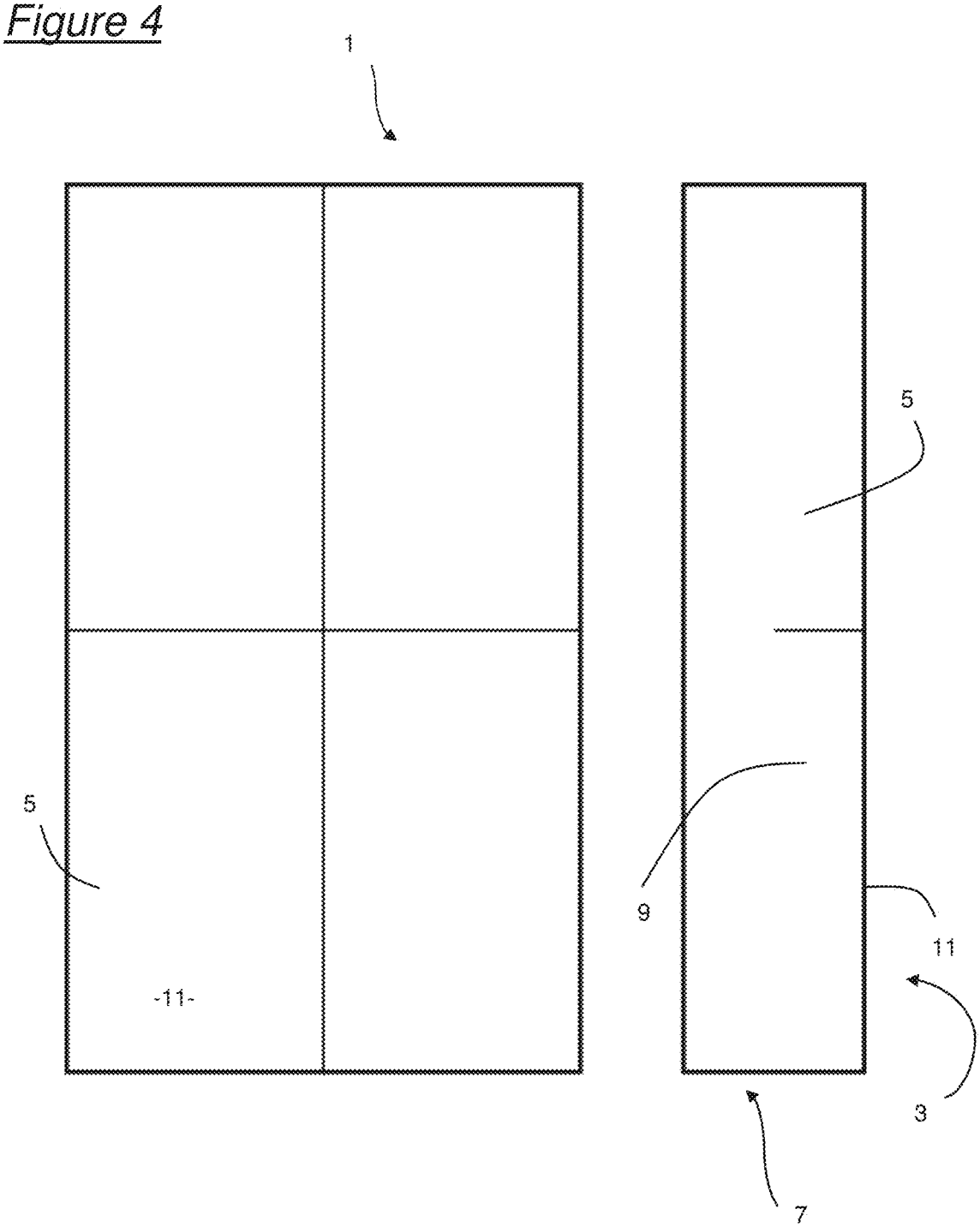
FIG. 4 is a schematic representation (plan view (left) and side view (right)) of a haemostatic sponge according to a less preferred embodiment of the invention.

A haemostatic sponge as shown in FIG. 4 has only four tissue-contacting elements, each with a significantly larger cross-sectional area than the sponges of FIGS. 1, 2 and 3. The tissue-contacting elements were formed by making a single incision width-wise and a single incision length-wise. Similar features to those in FIGS. 1, 2 and 4 have been assigned like reference numerals.

Example 1—Preparation of Surface Modified Gelatin Foam Sponges

Sample A: A sponge having the general form shown in FIG. 1 was prepared as follows. A series of incisions were made on a surface of gelatin foam sponges (GelitaSpon by Gelita) using a sharp razor blade (0.1 mm to 0.3 mm width) to create columnar or finger-like tissue-contacting elements on the surface. Incisions were made along the length at 0.5 mm to 2 mm intervals, and to a depth of about 5-8 mm, and a series of widthwise incisions were also made at 0.5 mm to 2 mm intervals at a depth of 5-8 mm. The result was the creation of tissue-contacting elements with substantially rectangular cross-sectional shapes, each having an end face with an area of 0.25 mm$^2$ to 4 mm$^2$. Each sponge had a length of about 30 mm, a width of about 20 mm and a thickness of about 10 mm.

Sample B: A sponge having the general form shown in FIG. 2 was prepared as follows. A series of incisions were made on a surface of gelatin foam sponges (GelitaSpon by Gelita) using a sharp razor blade (0.1 mm to 0.3 mm width) to create columnar or finger-like tissue-contacting elements on the surface. Incisions were made lengthwise at 0.5 mm to 2 mm intervals, and to a depth of about 1-2 mm, and a series of widthwise incisions were also made at 0.5 mm to 2 mm intervals, also to a depth of about 1-2 mm. The result was the creation of tissue-contacting elements with substantially rectangular cross-sectional shapes, each having an end face with an area of 0.25 mm$^2$ to 4 mm$^2$. Each sponge had a length of about 30 mm, a width of about 20 mm and a thickness of about 10 mm.

Sample C: A sponge having the general form as shown in FIG. 3 was prepared as follows. A series of incisions were made on a surface of gelatin foam sponges (GelitaSpon by Gelita) using a sharp razor blade (0.1 mm to 0.3 mm width) to create columnar or finger-like tissue-contacting elements on the surface. Incisions were made lengthwise at 0.5 mm to 2 mm intervals, and to a depth of about 5-8 mm, and a series of widthwise incisions were also made at 0.5 mm to 2 mm intervals, also to a depth of 5-8 mm. Further incisions were made diagonally through each tissue-contacting element to a depth of 5-8 mm to form a sponge with tissue-contacting elements having substantially triangular cross-sections and cross-sectional areas of approximately one quarter of those of Samples A and B. Each sponge had a length of about 30 mm, a width of about 20 mm and a depth of about 10 mm.

Sample D was the control sponge. No incisions were made in the surface of GelitaSpon (Gelita) sponges. Each sponge had a length of about 30 mm, a width of about 20 mm and a depth of about 10 mm.

Sample E: A sponge having the general form shown in FIG. 4 was prepared as follows. A single incision was made length-wise to a depth of about 5-8 mm and a single incision was made widthwise, also to a depth of about 5-8 mm, to create four tissue-contacting elements, each having an end face with an area of about 150 mm$^2$. Each sponge had a length of about 30 mm, a width of about 20 mm and a depth of about 10 mm.

Sample F: A sponge was prepared using an automated robotic blade to make lengthwise and widthwise incisions at 1.5 mm intervals. The incisions had a depth of 3 mm. By using an automated robotic blade, the process is much faster and the surface of a single 5×8 cm sponge could be modified in approximately 10 seconds.

Example 2—Scanning Electron Microscope Images of Surface-Modified Gelatin Foam Sponges Scanning Electron Microscope (SEM) images of the surfaces of the some of the samples were taken using a JEOL 6060LV variable pressure scanning electron microscope with a Leica EM SD005 sputter coater.

Figure 5:
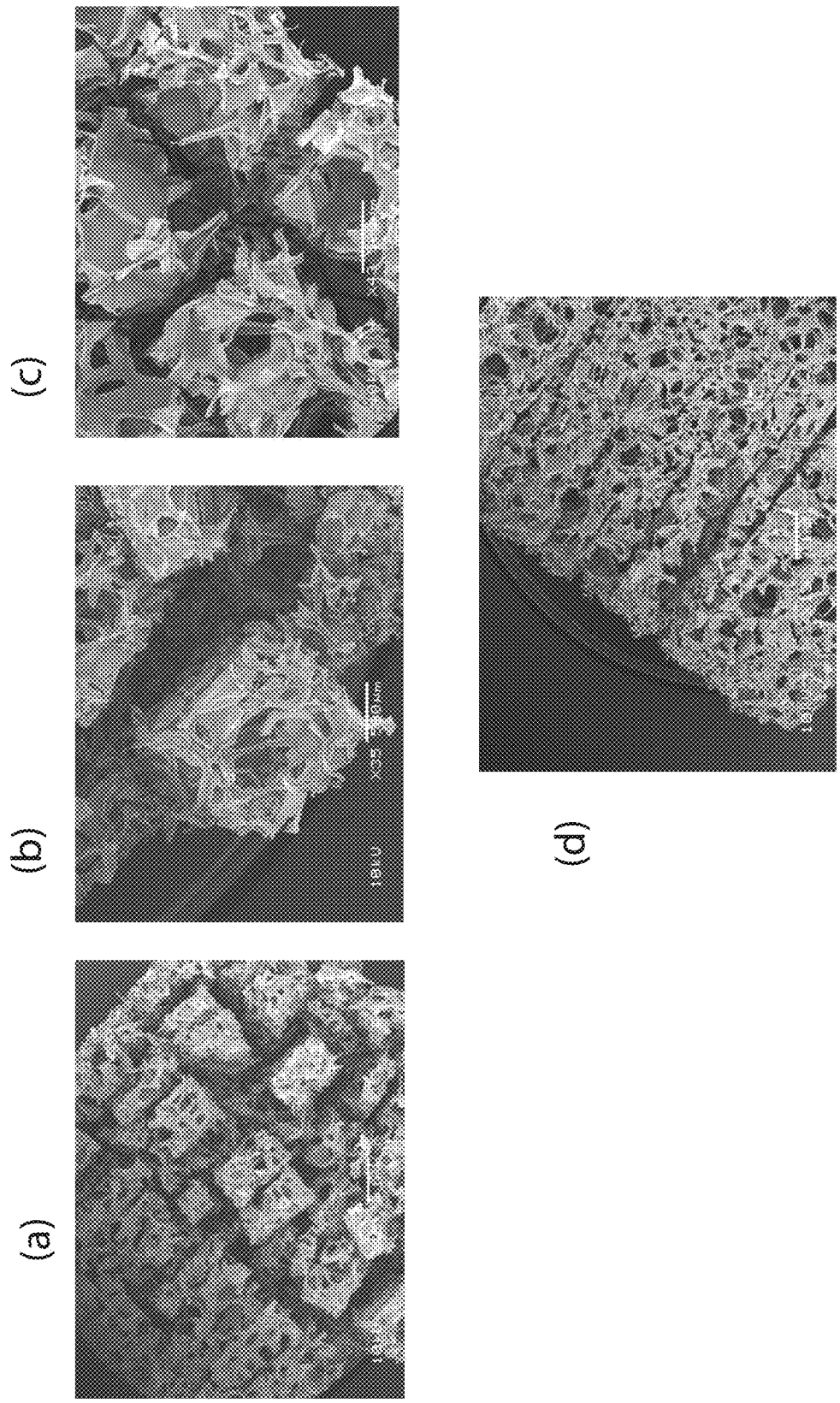
FIGS. 5a to 5d show SEM Images of a haemostatic sponge according to an embodiment of the invention.

FIGS. 5a, 5b and 5c show SEM images of Sample A (plan view) at various magnifications. The face of the tissue-contacting element in FIG. 5b has a surface area of approximately 1.5 mm$^2$.

FIG. 5d shows a SEM image (×13 magnification) of Sample A (side view) showing tissue-contacting elements with a depth of about 8 mm.

FIGS. 6a, 6b and 6c show SEM images of Sample B (plan view) at various magnifications.

FIG. 6d shows an SEM image (×14 magnification) of Sample B (side view) showing tissue-contacting elements with a depth of about 2 mm.

FIG. 7 shows an SEM image (×13 magnification) of Sample D (plan view).

Example 3—Testing Adhesion of the Surface-Modified Gelatin Sponges in a Surgical Procedure Rabbits (New Zealand White males weighing approximately 3 kg) were prepared and anaesthetised using standard procedures, and the liver uncovered. Biopsy punch holes (5 mm diameter and 4-5 mm deep) were made in the liver lobes, and Samples B and D (control) were placed on the wound and compressed for 1 minute with gauze. Lightly bleeding biopsy wounds were selected such that the sponges would not be fully soaked with blood when placed on the wound. After three minutes the sponge was lifted at one corner with forceps. A further control was also tested: Tachosil (Takeda), a collagen sponge with immobilised thrombin and fibrinogen. Each treatment was replicated three times and the observations were consistent.

Results

| Sponge | Image | Comment |
|---|---|---|
| Sample B | See FIGS. 8a and 8b | Adhesion is very strong. Lifting the sponge causes the liver to be pulled. The sponge stretches but remains attached to the liver. |
| Sample D | See FIGS. 9a and 9b | Adhesion is very weak. The sponge lifts off easily |
| Tachosil (collagen sponge with thrombin and fibrinogen) | See FIG. 10 | Good adhesion observed. Corner can be lifted in some cases but majority of sponge remains well adhered. |

Example 4—In Vitro Adhesion Tests 4.1 Experiment 1

Method:

A 1 cm diameter biopsy hole of 5 mm depth was punched out of lamb's liver (Marks & Spencer, UK). A solution of human plasma (0.1 ml, A1174 EXP-2016-10, Alpha Labs) was applied to the hole. All materials were heated to 37° C. prior to the experiment. Surface-modified Gelatin sponges (Gelita, Gelita Standard, Lot 101554/6), prepared to form Samples A, B and E (as described in Example 1) were applied face down onto and overlapping the biopsy hole, and compressed with cotton gauze for 1 minute. The plasma was added to the biopsy hole such that the sponges would not be fully soaked with plasma when placed onto the biopsy hole (to simulate a lightly bleeding wound). Using a pair of tweezers an attempt was made to lift the sponge by a corner. The level of adhesion was observed visually by comparison with control Sample D (i.e. an unmodified sponge).

Results:

The in vitro test was designed to mimic aspects of Example 3, and the overall results were broadly similar in that foam sponges without surface modification were not adhesive, and that those with finger-like tissue-contacting elements having an external surface area of 4 mm$^2$ or less were strongly adhesive. It was observed that the sponges with the longer tissue-contacting elements (Sample A) were more effective than those with the shorter tissue-contacting elements (Sample B) in vitro, but that the level of adhesion of the sponge with the longer tissue-contacting elements (Sample A) was not greater than that observed in the animal trial with a sponge of a shorter tissue-contacting elements (Sample B). In Experiment 3 (see below), Sample C demonstrated an improvement of adhesion.

The poor adhesion of Sample E shows that in some circumstances, sponges with larger tissue-contacting elements (e.g. with a cross-sectional area of approximately 150 mm$^2$) are less preferred. Sponges having tissue-contacting elements with a smaller cross-sectional area may be preferred in certain circumstances because they can result in stronger adhesion.

The in vitro test is therefore useful for testing permutations of the surface modification, and for optimisation of adhesion. For example, the various sizes and shapes of tissue-contacting elements, and types of sponge materials could be readily tested.

Figure 11:
FIG. 11 shows the in vitro adhesive properties of a commercially-available haemostatic sponge (Gelita)
Figure 12:
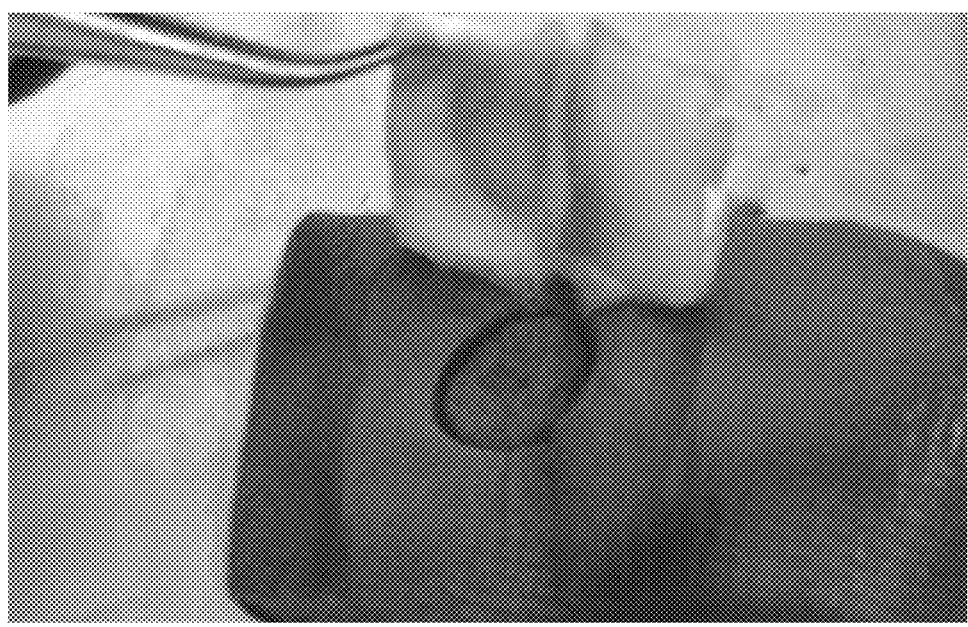
FIG. 12 shows the in vitro adhesive properties of a haemostatic sponge according to a less preferred embodiment of the invention.
Figure 13:
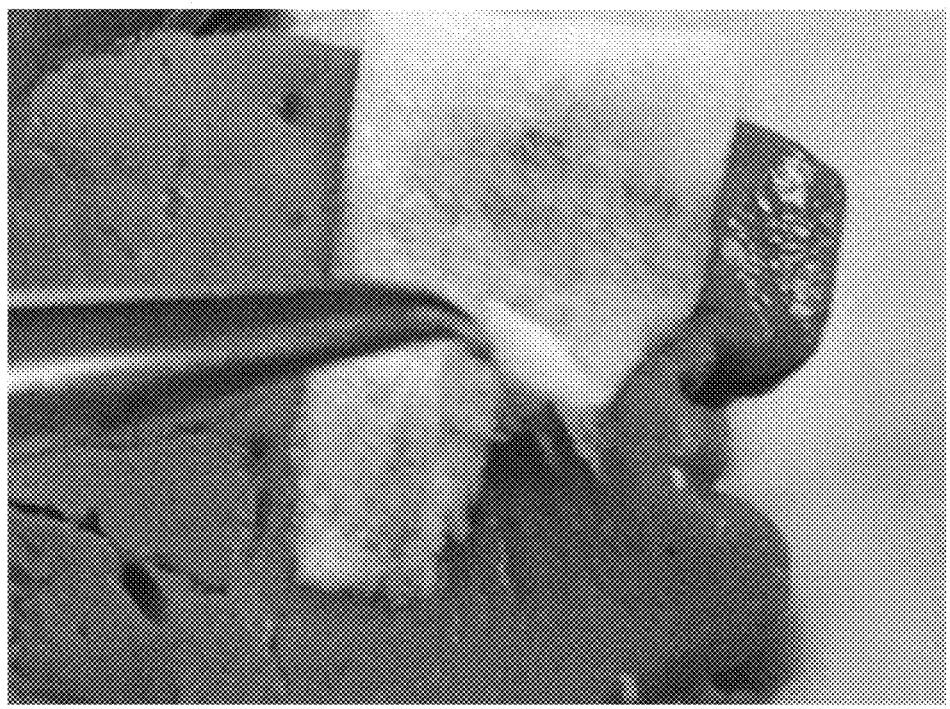
FIG. 13 shows the in vitro adhesive properties of a haemostatic sponge according to an embodiment of the invention.
Figure 14:
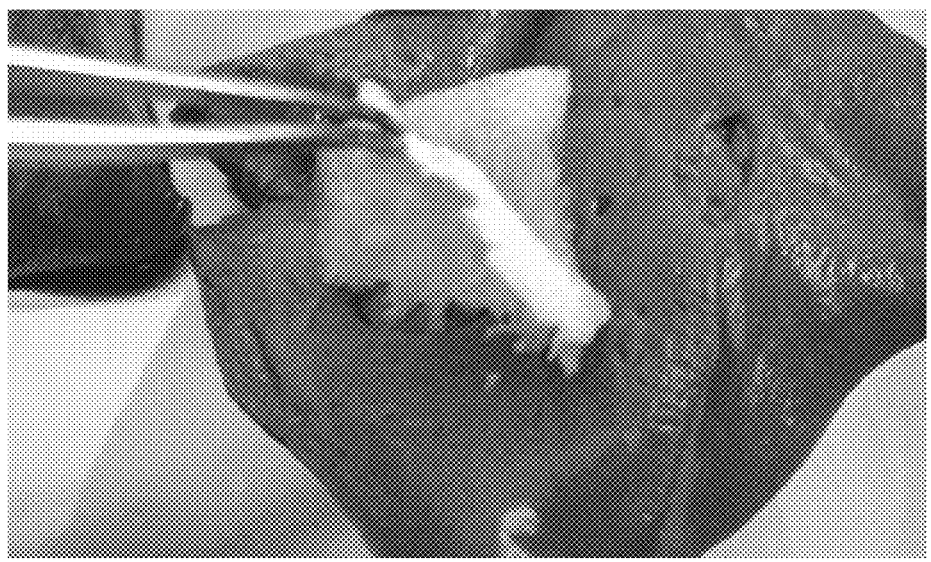
FIG. 14 shows the in vitro adhesive properties of a haemostatic sponge according to an embodiment of the invention.

| Sample Sponge | Images | Comment |
|---|---|---|
| Sample D | See FIG. 11 | Poor adhesion |
| Sample E | See FIG. 12 | Poor adhesion |
| Sample B | See FIG. 13 | Strong adhesion observed, as most of the sponge stayed in place when the corner was lifted |
| Sample A | See FIG. 14 | Strong adhesion observed. Improved adhesion compared to Sample B. The sponge had to be ripped from the surface leaving finger-like tissue-contacting elements attached |

4.2 Experiment 2

Method:

A 1 cm diameter biopsy hole of 5 mm depth was punched out of lamb's liver (Marks & Spencer, UK). A solution of deionised water (0.5 ml) was applied to the hole. All materials were at either at room temperature or heated to 37° C. prior to the experiment. The surface-modified Gelatin sponges (Gelita, Gelita Standard, Lot T01554/6), were prepared to form Sample C (as described in Example 1). The sponges were applied face down onto and overlapping the biopsy hole, and compressed with cotton gauze for 30 seconds. The water was added to the biopsy hole such that the sponges would not be fully soaked with water when placed onto the biopsy hole (to simulate a lightly bleeding wound). Adhesion was observed visually. The maximum force required to remove the sponge from the surface of the liver was also measured using a DGD-3 50G Gram Gauge (Mecmesin, Part No:890-003).

The level of adhesion was observed visually by comparison with control Sample D.

Results:
Room Temperature

| Sample D Maximum Force required to remove the sponge (G) | Sample C Maximum Force required to remove the sponge (G) |
|---|---|
| 5 | 15 |
| 5 | 16 |
| 6 | 16 |

37° C. Samples

| Sample D Maximum Force required to remove the sponge (G) | Sample C Maximum Force required to remove the sponge (G) |
|---|---|
| 40 | >60 |

Note: Gram Gauge's maximum force measurement is 60 g. The Sample C sponge exceeded this.

4.3 Experiment 3

Method:

A 1 cm diameter biopsy hole of 5 mm depth was punched out of lamb's liver (Marks & Spencer, UK). A solution of human plasma (0.1 ml, A1174 EXP-2016-10, Alpha Labs) was applied to the hole. All materials were heated to 37° C. prior to the experiment. The surface-modified Gelatin sponges (GelFoam, Pfizer and SpongoStan Standard, Ferrosan) and Collagen Sponges (Kolspon, Medira and Ultrafoam, Bard) were prepared to form Sample C (as described in Example 1). These were applied face down onto and overlapping the biopsy hole, and compressed with cotton gauze for 1 minute. The plasma was added to the biopsy hole such that the sponges would not be fully soaked with plasma when placed onto the biopsy hole (to simulate a lightly bleeding wound). Using a pair of tweezers an attempt was made to lift the sponge by a corner. The level of adhesion was observed visually by comparison with control Sample D (i.e. no modifications to the respective sponges).

Results:

| Sponge Sample | Control Sample D | Sample C | Comment |
|---|---|---|---|
| GelFoam | See FIG. 15a | See FIG. 15b | Sample C sponge significantly more adhesive than Sample D. |
| SpongoStan Standard | See FIG. 16a | See FIG. 16b | Sample C sponge significantly more adhesive than Sample D. Was able to pick whole liver piece up with Sample C. |
| KolSpon | See FIG. 17a | See FIG. 17b | Sample C sponge significantly more adhesive than Sample D. Was able to pick whole liver piece up with Sample C. |
| UltraFoam | See FIG. 18a | See FIG. 18b | Sample C sponge significantly more adhesive than Sample D. Was able to pick whole liver piece up with Sample C. |

4.4 Experiment 4

Comparison of the Adherence of a Modified Sponge with 1.5×1.5 mm Tissue-Contacting Elements Produced Using an Automated Robotic Blade (Sample F) Versus an Un-Modified Sponge.

Materials:

Spongostan gelatin foam sponges (Ferrosan MS0002)

Human fibrinogen @ 3 mg/ml (Enzyme Research Inc.) warmed to 37° C.

Ox liver (Marks & Spencer) cut into 5, 10 and 25 gram segments warmed to 37° C.

Method:

150 microlitres of fibrinogen was pipetted onto the surface of an ox liver segment. Three weights of ox liver were tested: 5, 10 and 25 grams. The modified and unmodified sponge test articles (1×2×1.4 cm) were compressed onto the pool of fibrinogen on the ox liver for 3 minutes, and then lifted to a height of approximately 30 cm. The duration over which the sponge held the ox liver was measured over a ten minute period.

Results:

The control sponge without surface modification held a 5 gram liver segment for 1 minute only, and failed to lift a 10 gram or 25 gram segment. In contrast, the modified sponge held a 25 gram liver segment for at least ten minutes, demonstrating the significantly increased adherence of the modified sponge in comparison with the unmodified sponge.

The invention claimed is:

1. A bioresorbable haemostatic foam sponge for adhering to a wound, the sponge comprising a tissue-contacting surface configured to contact the wound, which surface is divided into a plurality of closely-spaced tissue contacting elements such that there are at least 10 tissue contacting elements per 100 mm$^2$ of tissue-contacting surface, wherein the sponge is manufactured from collagen, starch, gelatin or hyaluronic acid, and wherein the tissue-contacting elements are columnar, the cross-sectional area of each tissue-contacting element is consistent throughout the depth of the tissue-contacting element, and the cross-sectional area of each face of each tissue contacting element is 50 mm$^2$ or less.

2. The haemostatic sponge according to claim 1 wherein each tissue contacting element has a depth of at least 2 mm.

3. The haemostatic sponge according to claim 1, wherein each tissue contacting element has a depth of 10 mm or less.

4. The haemostatic sponge according to claim 1, wherein the depth of each tissue contacting element is 80% or less of the depth of the sponge.

5. The haemostatic sponge according to claim 1, wherein the cross-sectional shape of each tissue contacting element is substantially rectangular.

6. The haemostatic sponge according to claim 1, wherein each face of each tissue contacting element has a cross-sectional area of 25 mm$^2$ or less.

7. The haemostatic sponge according to claim 1, wherein the maximum cross-sectional linear dimension of each tissue contacting element is 10 mm or less.

8. The haemostatic sponge according to claim 1, wherein the maximum cross-sectional linear dimension is two times or less than the depth of the tissue contacting element.

9. The haemostatic sponge according to claim 1, wherein the tissue contacting elements are arranged such that each tissue contacting element is within 1 mm of another tissue contacting element.

10. The haemostatic sponge according to claim 1, wherein the sponge has pores with a diameter of 3 mm or less.

11. The haemostatic sponge according to claim 1 which comprises an immobilised haemostatic agent.

12. The haemostatic sponge according to claim 11, wherein the haemostatic agent comprises a clotting factor.

13. The haemostatic sponge according to claim 11, wherein the haemostatic agent further comprises carriers on which a plurality of fibrinogen-binding peptides is immobilised.

14. The haemostatic sponge according to claim 1, comprising reactive chemical groups that can react to form covalent bonds when contacted with tissue.

15. The haemostatic sponge according to claim 1 in which the tissue contacting elements have been formed by cutting or incising a surface of a sponge.

16. The haemostatic sponge according to claim 1, wherein the sponge is manufactured from gelatin.

17. The haemostatic sponge according to claim 1, wherein the tissue contacting elements are arranged such that each tissue contacting element is within 0.1 mm of another tissue contacting element.

18. The haemostatic sponge according to claim 1, wherein at least 50% of the pores have a diameter between 1 and 1500 μm.

19. A method for forming the haemostatic sponge according to claim 1, comprising cutting or embossing a surface of a haemostatic sponge.

20. A method of controlling bleeding, comprising administering the haemostatic sponge according to claim 1, to a wound.

* * * * *